(12) United States Patent
Portney

(10) Patent No.: US 6,454,801 B1
(45) Date of Patent: Sep. 24, 2002

(54) PRIMARY AND SUPPLEMENTAL INTRAOCULAR LENS SYSTEM

(75) Inventor: Valdemar Portney, Tustin, CA (US)

(73) Assignee: Allergan, Waco, TX (US)

( * ) Notice: Subject to any disclaimer, the term of this patent is extended or adjusted under 35 U.S.C. 154(b) by 0 days.

(21) Appl. No.: 09/562,405

(22) Filed: May 1, 2000

Related U.S. Application Data

(62) Division of application No. 08/920,209, filed on Aug. 15, 1997, now Pat. No. 6,113,633, which is a continuation of application No. 08/592,754, filed on Jan. 26, 1996, now abandoned.

(51) Int. Cl.⁷ .................................................. A61F 2/16
(52) U.S. Cl. ...................................... 623/6.34; 623/6.32
(58) Field of Search ................................ 623/6.32, 6.34

(56) References Cited

U.S. PATENT DOCUMENTS

| | | |
|---|---|---|
| 4,338,687 A | 7/1982 | Rainin |
| 4,634,441 A | 1/1987 | Clayman et al. |
| 4,678,469 A | 7/1987 | Kelman |
| 4,684,014 A | 8/1987 | Davenport |
| 4,736,836 A | 4/1988 | Alongi et al. |
| 4,892,543 A | 1/1990 | Turley |
| 4,932,971 A | 6/1990 | Kelman |
| 4,963,148 A | 10/1990 | Sulc et al. |
| 5,026,396 A | 6/1991 | Darin |
| 5,030,231 A | 7/1991 | Portney |
| 5,041,134 A | 8/1991 | O'Donnell |
| 5,088,809 A | 2/1992 | Portney |
| 5,182,053 A | 1/1993 | Creasman et al. |
| 5,201,762 A | 4/1993 | Hauber |
| 5,222,981 A | 6/1993 | Werblin |
| 5,258,025 A | 11/1993 | Fedorov et al. |
| 5,358,520 A | * 10/1994 | Patel .......................... 623/6.34 |
| 5,366,502 A | 11/1994 | Patel |
| 5,480,428 A | 1/1996 | Fedorov et al. |

FOREIGN PATENT DOCUMENTS

| | | |
|---|---|---|
| DE | 3626869 | 8/1986 |
| DE | 4038088 | 11/1990 |
| EP | 0174917 | 3/1986 |
| EP | 0328117 | 8/1989 |
| EP | 0337390 | 10/1989 |
| EP | 0528325 | 2/1993 |
| FR | 8916885 | 6/1991 |
| FR | 2666735 | 3/1992 |
| WO | 8705797 | 10/1987 |
| WO | 9004512 | 5/1990 |
| WO | 9520926 | 8/1995 |

OTHER PUBLICATIONS

Article entitled Multipiece IOL seen as refractive tool, by leslie Sabbagh, Source Theodore PI Werbin, MD.

* cited by examiner

Primary Examiner—Dinh X. Nguyen
(74) Attorney, Agent, or Firm—Stout, Uxa, Buyan & Mullins; Frank J. Uxa

(57) ABSTRACT

A supplemental intraocular lenses may be attached to conventional primary intraocular lenses using annular wrap-around clamps or adhesive. New primary intraocular lens configurations have pockets for accommodating relatively small, supplemental intraocular lenses therein.

9 Claims, 2 Drawing Sheets

PRIMARY AND SUPPLEMENTAL INTRAOCULAR LENS SYSTEM

This application is a division of application Ser. No. 08/920,209 filed Aug. 15, 1997, now U.S. Pat. No. 6,113,633, which is a continuation of application Ser. No. 08/592,754 filed Jan. 26, 1996, now abandoned, the disclosure of which is incorporated in its entirety herein by reference.

FIELD OF THE INVENTION

This invention relates generally to intraocular lenses and:, more particularly, to supplemental intraocular lenses, which can be placed in or on primary intraocular lenses to thereby change the effective optical power of the primary intraocular lens.

BACKGROUND OF THE INVENTION

Vision is achieved in the human eye by transmitting an image through a clear outer portion called the cornea, and focusing this image via a natural lens onto a retina. When the natural lens looses its ability to clearly focus the image onto the retina through, for example, cataracts or injury, the quality of the focused image on the retina can be severely compromised.

An accepted treatment for a damaged natural lens is surgical removal of the natural lens and replacement of the natural lens with an artificial intraocular lens. One way to accomplish this procedure is to form a relatively long incision in the eye and remove the natural lens in one piece. A more popular method for removing the natural lens is to form a shorter incision in the eye and insert a probe or a phaco tip of a phacoemulsification instrument through the incision into the eye to break up the natural lens using ultrasonic energy. The lens fragments can then be aspirated from the natural eye through the relatively short phaco incision, and the phaco tip is then removed.

A preferred conventional method of removing a natural lens is accompanied with a subsequent implantation of a replacement intraocular lens in the same surgical procedure. A typical intraocular lens includes an optic usually having a diameter of about 6 mm, and fixation members coupled to (or formed with) the optic to fix the optic within the eye in the region of the extracted natural lens. These fixation members are generally in the form of at least two haptics, which may be flexible, elongated, open-ended loops that project from the edge of an optic portion of the intraocular lens. The fixation member may require additional incision links, depending upon the number, length, and configuration of the fixation member.

Intraocular lenses can be of two basic types, those having a hard or rigid optic formed, for example, of polymethylmethacrylate (PMMA) and those having a deformable optic which is constructed of a deformable material such as silicone, hydrogel, or an acrylic. When a hard intraocular lens is used, the small phaco incision must be enlarged to approximately the diameter of the hard optic, in order to permit the hard optic to be inserted through the incision. A deformable optic, on the other hand, may have a high elongation so that the optic can be causes to resiliently stretch and flex to assume a small cross-sectional configuration for passage through a small phaco incision.

Before implanting the intraocular lens, the physician must determine the intraocular lens power needed to achieve the desired refraction needs of the patient. This procedure can be difficult and inexact. Errors in measurement, inaccuracy of assumptions, and the difficulty of achieving precise placement of an intraocular lens make the physician's selection of an exact corrective power highly prone to inaccuracies. Post-operative changes to the patient's eye may also change the refractive power needed for the intraocular lenses in the patient. Consequently, the intraocular lens, after implantation, does not always provide a perfect vision correction. These post-operative refractive errors must often be corrected by a subsequent surgery to replace the implanted intraocular lens with another intraocular lens. A subsequent surgery involves re-entry into the eye through a new incision, removal of the initial intraocular lens, and implantation of a new intraocular lens. Needless to say, this conventional subsequent surgery procedure can be traumatic to the eye.

One approach for limiting the amount of trauma on the human eye caused by subsequent replacement of the intraocular lens is disclosed in Patel U.S. Pat. No. 5,366,502. This patent discloses supplemental intraocular lenses which may be subsequently attached to primary intraocular lenses after the initial implantation of the primary intraocular lens. Addition of a supplemental intraocular lens to a primary intraocular lens does not entail removal of the primary intraocular lens, and further requires a relatively small incision in the eye. The supplemental intraocular lenses, and most of the primary intraocular lenses, of this patent include specially configured connectors for mating the supplemental intraocular lens to the implanted, primary intraocular lens. These connectors can be in the form of hooks, projections, slots, and loops, which are suitable for securing the supplemental intraocular lens to the primary intraocular lens. These various securing means, however, can be complex and difficult to manufacture and implement. Additionally, the sizes of these supplemental intraocular lenses are often unnecessarily large, thus requiring a larger incision and more trauma to the eye.

SUMMARY OF THE INVENTION

New supplemental intraocular lenses and new primary intraocular lenses have been discovered. The present supplemental intraocular lenses may be attached to, conventional primary intraocular lenses, for example, using annular wrap-around clamps or adhesive. Thus, no special connectors need be included on the primary intraocular lens. This is a substantial advantage since the present supplemental intraocular lenses can be attached or secured to any primary intraocular lens. The primary intraocular lens need not be specially configured to accept the supplemental intraocular lens. Put another way, the primary intraocular lens need not be constructed to anticipate that a supplemental intraocular lens will be used. In addition, new primary intraocular lenses which have pockets for accommodating relatively small, supplemental intraocular lenses therein, and such small, supplemental intraocular lenses are provided. The present supplemental intraocular lenses are relatively easy to insert in the eye since, for example, they are relatively small and/or have no independent structure effective to fix the supplemental intraocular lens in the eye.

In one broad aspect, the present invention is directed to a supplemental intraocular lens including a central optic portion having at least one dioptic power, a peripheral zone surrounding the optic portion, and an added peripheral zone having wrap-around clamps for securing the supplemental intraocular lens to the primary intraocular lens. The primary intraocular lens may be conventional, for example, having no structure or structures specifically adapted to connect or couple with the supplemental intraocular lens. The optic portion and the peripheral zone of the supplemental intraocular lens contact a first primary intraocular lens face, and the wrap-around clamps contact a second primary intraocular lens face, which is substantially opposite to the first primary intraocular lens face. The peripheral zone can be slightly stretched to facilitate application of the wrap-around clamps around the periphery of the primary intraocular lens, and the wrap-around clamps are relatively rigid to facilitate a secure fit of the supplemental intraocular lens onto the primary intraocular lens. One or more, for example, two apertures formed in the supplemental intraocular lens accommodate the fixation member or members of the primary intraocular lens, to thereby prevent rotation of the supplemental intraocular lens, thus facilitating cylinder corrections.

According to another broad aspect of the present invention, the supplemental intraocular lens includes only a central optic portion and a peripheral zone. The peripheral zone has substantially no optical power, and has a reduced thickness relative to the thickness of a periphery of the optic portion. The supplemental intraocular lens is placed onto the first primary intraocular lens face, and the outer annular portion of the peripheral zone is attached to the first primary intraocular lens face. The outer annular portion of the peripheral zone may be secured to the first primary intraocular lens face using an adhesive. This supplemental intraocular lens may be replaced with a second intraocular lens by removing all of the first supplemental intraocular lens, except for the outer annular portion of the peripheral zone, and then placing the second supplemental intraocular lens, having a slightly smaller diameter, onto the first primary intraocular lens face.

In another broad aspect of the present invention, the primary intraocular lens has a pocket for accommodating the supplemental intraocular lens. The pocket is configured to expand upon insertion of the supplemental intraocular lens, to thereby reshape and change the refractive power of the primary intraocular lens. The supplemental intraocular lenses used for insertion into the pockets may be relatively small, and may have either convex or concave surfaces, or both.

These and other aspects of the present invention are apparent in the following detailed description and claims, particularly when considered in conjunction with the accompanying drawings in which like parts bear like reference numerals.

DETAILED DESCRIPTION OF THE PRESENTLY PREFERRED EMBODIMENTS

Figure 1:
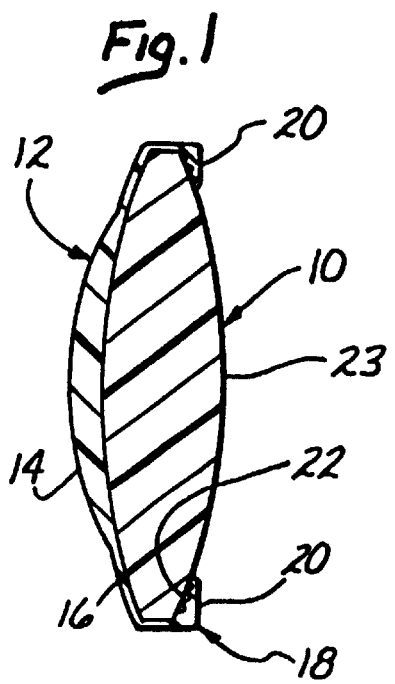
FIG. 1 is a cross-sectional view of a wrap-around supplemental intraocular lens, coupled to a primary intraocular lens, according to a first preferred embodiment.
Figure 2:
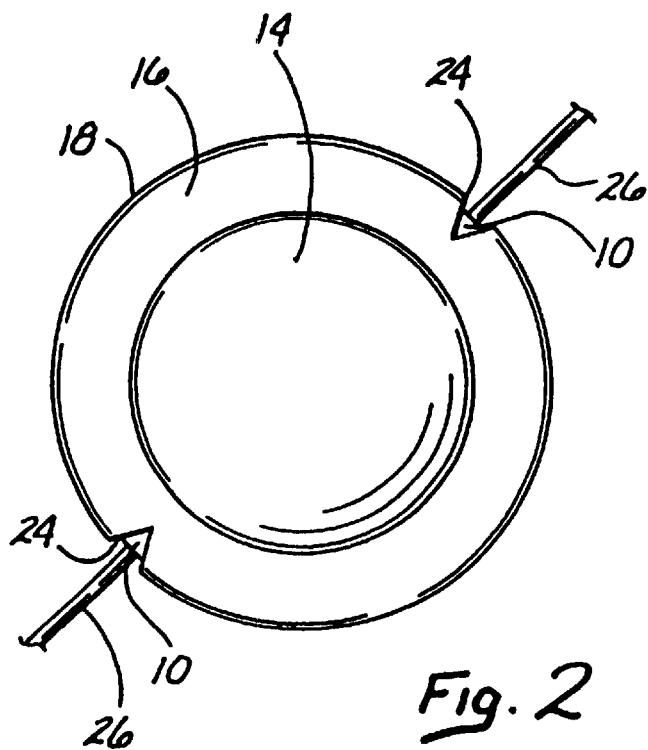
FIG. 2 is a top planar view of a wrap-around supplemental intraocular lens, coupled to a primary intraocular lens, according to the first preferred embodiment.

FIG. 1 shows a wrap-around supplemental intraocular lens 12 attached to a primary intraocular lens 10. The primary intraocular lens 10 is secured within the eye using two conventional fixation members 26 (FIG. 2). Any reasonable number of fixation members 26 may be used to secure the primary intraocular lens 10 within the eye.

The primary intraocular lens 10 can be combined with the wrap-around supplemental intraocular lens 12 in the form of a multi-focal optic, for example, either at the time of initial surgical implant or later. The wrap-around supplemental intraocular lens 12 may be initially implanted with a multi-focal power, for example. If the patient cannot tolerate the multi-focal lens, or if the vision needs changing, the particular supplemental intraocular lens 12 may subsequently be replaced. The wrap-around supplemental intraocular lens 12 does not have fixation members 26 and, accordingly, can be removed or replaced much easier than the primary intraocular lens 10, thus reducing trauma to the eye. If the physician initially does not implant the correct primary intraocular lens 10, or if subsequent complications render the primary intraocular lens 10 insufficient, a second wrap-around supplemental intraocular lens 12 may be subsequently surgically implanted to correct the patient's vision.

The wrap-around supplemental intraocular lens 12 preferably comprises an optic portion 14 having at least one optic power and a periphery, and a peripheral zone 16 connected to the optical portion 14. The peripheral zone 16 preferably has substantially no optical power, and has a reduced thickness, relative to the thickness of the periphery of the optical portion 14. This reduced thickness of the peripheral zone 16 allows the peripheral zone 16 to stretch, according to one embodiment, when the wrap-around supplemental intraocular lens 12 is attached onto the primary intraocular lens 10. As presently preferred, the peripheral zone 16 stretches when the additional peripheral zone 18 is placed around the outer perimeter of the primary intraocular lens 10. The semi-rigid annular lips 20 preferably have bellows 22 for frictionally contacting the surface 23 of the primary intraocular lens 10.

As shown in FIG. 2, the additional peripheral zone 18 preferably fits around most of the outer perimeter of the primary intraocular lens 10. In alternative embodiments, however, the additional peripheral zone 18 may comprise a plurality of tabs or strips contacting the surface 23. For example, the additional peripheral zone 18 may comprise two small tabs. As another example, these two small tabs may have apertures 24 for accommodating the fixation members 26.

The wrap-around supplemental intraocular lens 12 may correct spherical refraction error, cylinder, and presbyopia. If the wrap-around supplemental intraocular lens 12 has cylinder correction, it is important that it not rotate. The two apertures 24 can be placed in the additional peripheral zone 18 to accommodate the two fixation members 26. If a different number of fixation members 26 is used on the primary intraocular lens 10, a corresponding number of apertures 24 may be used to accommodate those fixation members 26.

The apertures 24 may be pre-cut into the wrap-around supplemental intraocular lens 12 or, alternatively, may be cut by the physician at the time of the implant of the wrap-around supplemental intraocular lens 12. As presently. embodied, an incision of approximately one millimeter is needed to insert the wrap-around supplemental intraocular lens 12 into the eye for attachment to the primary intraocular lens 10.

Figure 3:
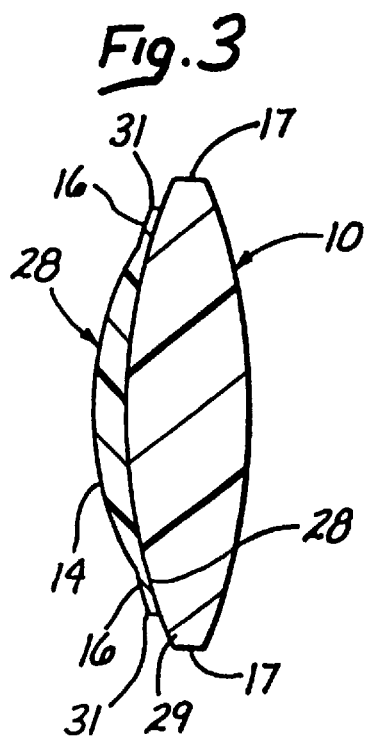
FIG. 3 is a cross-sectional view of a adhesion-type supplemental intraocular lens, attached to a primary intraocular lens, according to a second preferred embodiment.
Figure 4:
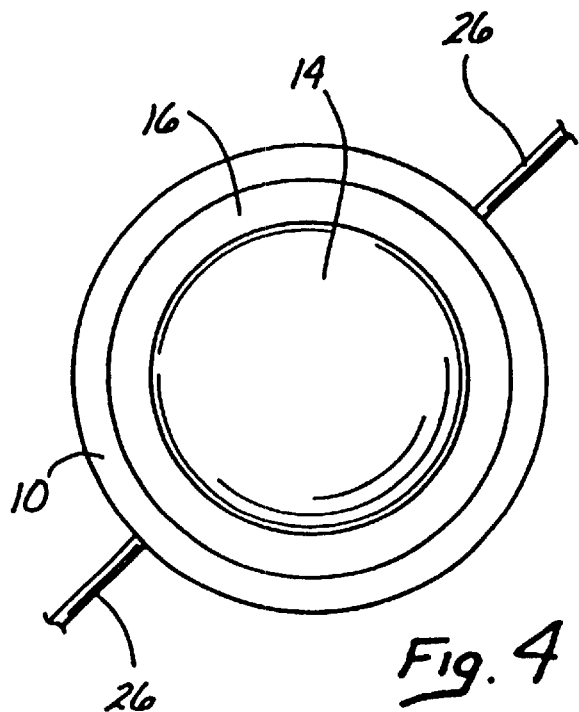
FIG. 4 is a top planar view of a adhesion-type supplemental intraocular lens, attached to a primary intraocular lens, according to the second preferred embodiment.

FIG. 3 shows the adhesion-type supplemental intraocular lens 28 attached to the surface 29 of the primary intraocular lens 10. The adhesion-type supplemental intraocular lens 28 comprises an optic portion 14, which is surrounded by a peripheral zone 16. As presently embodied, the peripheral zone 16 does not extend onto the outer peripheral zone 17 of the primary intraocular lens 10. FIG. 4 shows a top plan view of the adhesion-type supplemental intraocular lens 28 attached to the primary intraocular lens 10. Similarly to the embodiment of FIGS. 1 and 2, the peripheral zone 16 preferably comprises substantially no optical power and a reduced thickness, relative to the thickness of a periphery of the optic portion 14 of the adhesion-type supplemental intraocular lens 28. This peripheral zone 16 preferably completely surrounds the central optic portion 14, but may comprise tabs or strips, similarly to the embodiment of FIGS. 1 and 2. As presently preferred, this peripheral zone 16 surrounds at least 20% of the central optical portion 14.

Although the peripheral zone 16 preferably does not extend on to the outer peripheral edge 17 of the primary intraocular lens 10, other embodiments may have a peripheral: zone 16 extending onto the peripheral edge 17. The preferred configuration of the central optic portion 14 at least partially surrounded by the peripheral zone 16 allows for a very small supplemental intraocular lens 28 with simple construction. Accordingly, the presently preferred adhesion-type supplemental intraocular lens 28 may be inserted into the eye through a very small incision of less than one millimeter.

As presently embodied, the outer ends 31 of the peripheral zone 16 are attached to the face of the primary intraocular lens 10. A biological glue, for example, may be used for this attachment. The peripheral zone 16, surrounding at least 20% of the optic portion 14, according to the presently preferred embodiment, provides sufficient surface area for a secure adhesion.

Since only the outer ends 31 of the peripheral zone 16 are adhered to the face of the primary intraocular lens 10, the majority of the adhesion-type supplemental intraocular lens 28 may be severed and removed, leaving only the adhered outer ends 31. A second adhesion-type supplemental intraocular lens 28 may then be placed on the face of the primary intraocular lens 10. This second adhesion-type supplemental intraocular lens 28 preferably has a slightly smaller diameter, to compensate for the remaining outer ends 31 of the first adhesion-type supplemental intraocular lens 28. Alternatively, the second adhesion-type supplemental intraocular lens 28 may have a larger diameter, or may have peripheral zones 16 in different locations along the outer perimeter of the optic portion 14. When the diameter of the second adhesion-type supplemental intraocular lens 28 is larger than the diameter of the first adhesion-type supplemental intraocular lens 28, the peripheral zone 16 of the second adhesion-type supplemental intraocular lens 28 may overlap the remaining outer ends 31 of the first adhesion-type supplemental intraocular lens 28. As shown in FIG. 4, the adhesion-type supplemental intraocular lens 28 easily fits onto the face of the primary intraocular lens 10, and preferably has a correspondingly smaller diameter and area than that of the primary intraocular lens 10.

Figure 5:
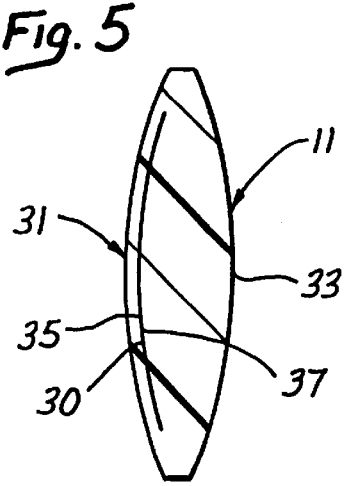
FIG. 5 is a cross-sectional view of a pocket primary intraocular lens according to a third preferred embodiment.

FIG. 5 shows the pocket primary intraocular lens 11 according to a third presently preferred embodiment. The pocket primary intraocular lens 11 comprises a pocket 30, which preferably is positioned close to either the front surface 31 or the rear surface 33 of the primary pocket intraocular lens 11. The pocket 30 preferably comprises a "clean" slice through a portion of the pocket primary intraocular lens 11 but, alternatively, may comprise other configurations. For example, the two interior walls 35 and 37 may have rugged or bellowed surfaces to assure, for example, that these two walls 35, 37 do not move relative to one another when the supplemental intraocular lens 32 (FIG. 6) is not in the pocket 30.

Figure 6:
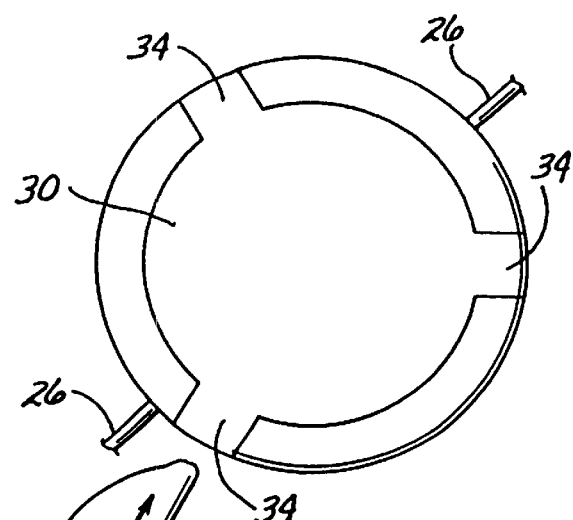
FIG. 6 is a top planar view of the pocket primary intraocular lens, showing insertion of the supplemental intraocular lens therein, according to the third preferred embodiment.

As shown in FIG. 6, the supplemental intraocular lens 32 can be folded and held with a pair of stainless steel folding forceps 36. The supplemental intraocular lens 32 is moved in the direction of arrow A1 into one of the pocket openings 34 of the pocket primary intraocular lens 11. In embodiments where the supplemental intraocular lens 32 is not folded, the pocket openings 34 are larger. The pocket primary intraocular lens 11 preferably comprises three pocket openings 34, but any reasonable number of pocket openings 34 may be configured according to preference.

Figure 7:
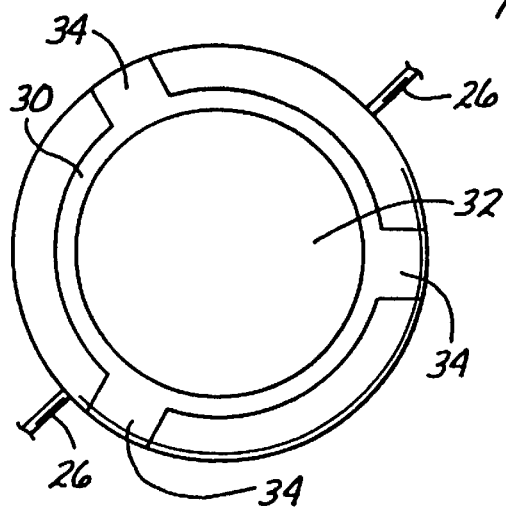
FIG. 7 is a top planar view of the pocket primary intraocular lens with the supplemental intraocular lens inserted therein, according to the third preferred embodiment.

FIG. 7 shows the supplemental intraocular lens 32 unfolded and centered within the pocket 30. As presently embodied, a good frictional fit is achieved between the surfaces of the supplemental intraocular lens 32 and the walls 35 and 37 of the pocket 30. If desired, other means of providing a snug and frictional fit between the supplemental intraocular lens 32 and pocket primary intraocular lens 11 may be implemented.

Figure 8:
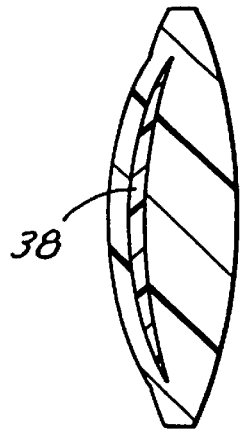
FIG. 8 is a cross-sectional view of a convex/concave supplemental intraocular lens within the pocket primary intraocular lens, according to the third preferred embodiment.
Figure 9:
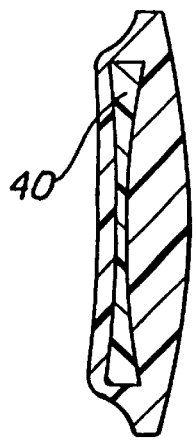
FIG. 9 is a cross-sectional view of a concave/concave supplemental intraocular lens within a pocket primary intraocular lens, according to the third preferred embodiment.

FIG. 8 illustrates a concave/convex supplemental intraocular lens 32 within the pocket 30, and FIG. 9 illustrates a concave/concave supplemental intraocular lens 40 within the pocket 30. The concave/convex supplemental intraocular lens 38 may be placed within the pocket 30 to reduce a refractive power, and the concave/concave supplemental intraocular lens 40 may be placed within the pocket 32 to increase a refractive power, for example. A variety of other configurations of the supplemental intraocular lens 32, for example, may be used within the pocket 30. As one example, a multi-focal supplemental intraocular lens 32 may be placed within the pocket 30. An important feature of this third embodiment is to reshape the primary pocket intraocular lens 11 through insertion of a supplemental intraocular lens 32 into the pocket 30.

While this invention has been described with respect to various specific examples and embodiments, it is to be understood that the invention is not limited thereto and that it can be variously practiced within the scope of the following claims.

What is claimed is:

1. A supplemental intraocular lens comprising an optic portion adapted for use in an eye and having at least one optical power, the supplemental intraocular lens including no structure effective to independently fix the position of the supplemental intraocular lens in the eye, the optic portion being sized and adapted to fit within a primary intraocular lens to thereby provide supplemental vision correction to the eye in which the primary intraocular lens is located.

2. The supplemental intraocular lens according to claim 1, wherein the optic portion being shaped to fit within a pocket of a primary intraocular lens.

3. A supplemental intraocular lens comprising an optic portion having at least one optical power, the optic portion sized and adapted to fit within a pocket of a primary intraocular lens to thereby provide a supplemental vision correction to the primary intraocular lens.

4. A primary intraocular lens having at least one optical power, and having a pocket for accommodating a supplemental intraocular lens to thereby modify the optical power of the primary intraocular lens.

5. The primary intraocular lens according to claim 1, wherein the primary intraocular lens comprises a first primary intraocular-lens face and a second primary intraocular-lens face, and wherein the pocket is located between the first primary intraocular-lens face and the second primary intraocular-lens face.

6. The primary intraocular lens according to claim 5, wherein the pocket comprises a pocket anterior surface located between the first primary intraocular-lens face and the second primary intraocular-lens face, and also comprises a pocket posterior surface located between the first primary intraocular-lens face and the second primary intraocular-lens face, the pocket anterior surface and the pocket posterior surface together forming the pocket within the primary intraocular lens for accommodating the supplemental intraocular lens.

7. The primary intraocular lens according to claim 6, wherein the pocket anterior surface and the pocket posterior surface contact one another before insertion of the supplemental intraocular lens into the pocket of the primary intraocular lens, and wherein insertion of the supplemental intraocular lens into the pocket of the primary intraocular lens separates the pocket anterior surface from the pocket posterior surface.

8. The primary intraocular lens according to claim 7, wherein the pocket anterior surface and the pocket posterior surface are joined together along respective circumferences of the pocket anterior surface and the pocket posterior surface, and wherein the supplemental intraocular lens is inserted into the pocket of the primary intraocular lens through an area along the respective circumferences of the pocket anterior surface and the pocket posterior surface that is not joined together.

9. The supplemental intraocular lens according to claim 7, wherein the pocket of the primary intraocular lens has three areas along the respective circumferences of the pocket anterior surface and the pocket posterior surface that are not joined together, and wherein the supplemental intraocular lens can be inserted into the pocket of the primary intraocular lens through any one of the three areas.

* * * * *

UNITED STATES PATENT AND TRADEMARK OFFICE
CERTIFICATE OF CORRECTION

PATENT NO. : 6,454,801 B1  
DATED : September 24, 2002  
INVENTOR(S) : Portney

Page 1 of 1

It is certified that error appears in the above-identified patent and that said Letters Patent is hereby corrected as shown below:

Column 1,
Line 12, "and:," should read -- and, --.

Column 5,
Line 11, "presently." should read -- presently --.

Column 7,
Line 5, "being shaped" should read -- is shaped --.
Line 16, "according to claim 1," should read -- according to claim 4, --.

Column 8,
Line 22, "The supplemental intraocular lens according to claim 7," should read -- The primary intraocular lens according to claim 8, --.

Signed and Sealed this

Seventeenth Day of June, 2003

JAMES E. ROGAN
*Director of the United States Patent and Trademark Office*